United States Patent [19]

Bader et al.

[11] 4,187,225
[45] Feb. 5, 1980

[54] NOVEL SYNTHESIS OF BIS PYRAZOLONE OXONOL DYES

[75] Inventors: Henry Bader, Newton Center; Michael H. Feingold, Randolph, both of Mass.

[73] Assignee: Polaroid Corporation, Cambridge, Mass.

[21] Appl. No.: 883,182

[22] Filed: Mar. 3, 1978

[51] Int. Cl.$^2$ .................... C07D 23/42; C09B 23/02
[52] U.S. Cl. .................... 260/239.9; 260/397.7 R; 430/522
[58] Field of Search .................... 260/239.9, 397.7 R

[56] References Cited

U.S. PATENT DOCUMENTS

| | | | |
|---|---|---|---|
| 3,839,325 | 10/1974 | Hoffstadt | 260/239.7 |
| 3,933,798 | 1/1976 | Curtis et al. | 260/239.9 |

OTHER PUBLICATIONS

Bader et al., J. Org. Chem. vol. 31, pp. 2319 to 2321 (1966).

*Primary Examiner*—John D. Randolph
*Attorney, Agent, or Firm*—Sybil A. Campbell

[57] ABSTRACT

In one embodiment, this application is directed to an improved method of synthesizing certain bis-pyrazolone oxonol compounds useful as antihalation dyes in photography which method comprises synthesizing a pyrazolone ethyl ester by reacting a p-N-alkylsulfonamidophenylhydrazine or its hydrochloride and sodium diethyl oxalacetate, hydrolyzing the pyrazolone ethyl ester thus formed to give the corresponding pyrazolonecarboxylic acid, esterifying the pyrazolonecarboxylic acid with a glycol to give the corresponding pyrazolone hydroxyalkyl ester and condensing said pyrazolone hydroxyalkyl ester with an aldehyde dianil hydrochloride to yield the dye product.

In another embodiment, the p-N-alkylsulfonamidophenylhydrazine is prepared by reacting p-fluorobenzenesulfonyl chloride and a primary alkylamine to yield the corresponding 1-fluoro-4-N-p-alkylsulfonamidobenzene and then reacting said alkylsulfonamidobenzene with hydrazine hydrate to yield the corresponding p-N-alkylsulfonamidophenylhydrazine which may be converted to its hydrochloride salt by reaction with a solution of hydrochloric acid.

33 Claims, No Drawings

NOVEL SYNTHESIS OF BIS PYRAZOLONE OXONOL DYES

BACKGROUND OF THE INVENTION

1. Field of the Invention

This invention relates to an improved method of synthesizing certain bis-pyrazolone oxonol compounds useful as antihalation dyes in photographic products and processes.

2. Description of the Prior Art

Photographic light-sensitive elements are often provided with antihalation layers for the purpose of absorbing reflected, scattered and/or diffused light which may adversely affect the quality of the image reproduced. Generally, such layers comprise organic dyes possessing the desired spectral absorption characteristics dispersed in a suitable matrix. Among the various types of dyes that have been employed for this purpose are pyrazolone dyes.

U.S. Pat. No. 3,933,798 of Harris L. Curtis and James W. Foley discloses and claims a class of bis-pyrazolone oxonol dyes wherein each of the two pyrazolone nuclei are substituted in the 1-position with an alkylsulfonamidophenyl moiety and substituted in the 3-position with an ester group of the formula

wherein Z is hydrogen, hydroxy or lower alkoxy and m is an integer 2 or 3. As discussed therein, these dyes may be synthesized by condensing 2 moles of the selected pyrazolone ester having an active methylene group in the pyrazolone ring and 1 mole of glutaconaldehyde dianil or malonaldehyde dianil in the presence of a condensing agent, such as triethylamine or pyridine. Also, they may be synthesized by employing ester interchange reactions to convert one dye to different dye products containing different ester groups.

Using either of these procedures in the preparation of the aforementioned dyes wherein Z of the ester group is hydroxy, it has been customary to employ a trans-esterification reaction (ester interchange reaction) to introduce the hydroxyalkyl ester into the starting pyrazolone or into the final dye product. For example, such dyes possessing a 3-carb($\beta$-hydroxy)ethoxy substituent have been synthesized by reacting an N-alkylsulfanilamide as a diazonium salt with diethylacetylsuccinate to give a 3-carbethoxy-1-(N-alkylsulfonamidophenyl)-2-pyrazolin-5-one which is converted by trans-esterification to the corresponding 3-carb($\beta$-hydroxy)ethoxy compound for reaction with glutaconaldehyde dianil or by synthesizing a bis-1,5-[3-carbethoxy-1-(N-alkylsulfonamidophenyl)-2-pyrazolin-5-one]-pentamethine oxonol dye precursor and converting it by trans-esterification to the corresponding [3-carb($\beta$-hydroxy)ethoxy-1-(N-alkylsulfonamidophenyl)-2-pyrazolin-5-one]-pentamethine oxonol dye.

Though these prior procedures are useful for synthesizing small amounts of the bis-hydroxyalkyl ester dyes on a laboratory scale, they do not lend themselves to the production of large quantities. Because the pyrazolone ethyl esters, i.e., the 3-carbethoxy-1-(N-alkylsulfonamidophenyl)-2-pyrazolin-5-ones are obtained as gummy semi-solids of varying purity, they are difficult to isolate and purify without considerable loss of material which results in low overall yields of dye product. If the pyrazolone ethyl esters are not isolated and purified, condensation with glutaconaldehyde dianil gives unstable bis-pyrazolone ethyl ester dye precursors for use in the subsequent trans-esterification step. Where the trans-esterification step is conducted prior to condensation with glutaconaldehyde dianil, the hydroxyethyl pyrazolone ester produced is highly impure and can be recovered only with difficulty and in poor yields.

The present invention provides an improved method of synthesizing the desired bis-pyrazolone hydroxyalkyl ester dyes in high purity and in at least twice the overall yields obtained previously, i.e., 40–45% yield versus the 15-20% yield obtained using the aforementioned procedures. This is accomplished by synthesizing the pyrazolone ethyl ester from a p-N-alkylsulfonamidophenylhydrazine and sodium diethyl oxalacetate and then hydrolyzing the pyrazolone ethyl ester in situ to give the corresponding carboxy acid which may be readily isolated and purified prior to esterification with the appropriate glycol. The hydroxyalkyl ester formed from the acid is then condensed with the selected aldehyde dianil hydrochloride to yield the bis-hydroxyalkyl ester pyrazolone oxonol dye.

It also has been discovered that the phenylhydrazine employed for reaction with the sodium diethyl oxalacetate can be synthesized in consistently high yields by nucleophilic displacement of activated fluorine. Though facile nucleophilic displacement of aromatic fluorine compounds activated by o- and p- electron-withdrawing groups was found to occur in dipolar aprotic solvents, as reported by H. Bader et al, *J. Org. Chem.*, 31, 2319 (1966), the only nucleophiles used were primary and secondary aliphatic amines. In the subject invention, a 1-fluoro-4-N-p-alkylsulfonamidobenzene prepared from p-fluorobenzenesulfonyl chloride and the desired alkylamine is reacted with hydrazine hydrate in an aprotic solvent to yield the corresponding p-N-alkylsulfonamidophenylhydrazine.

SUMMARY OF THE INVENTION

It is, therefore, the primary object of the present invention to provide a method of synthesizing certain bis-1,5-[3-carb($\beta$-hydroxy)alkoxy-1-(p-N-alkylsulfonamidophenyl)-2-pyrazolin-5-one]oxonol compounds useful as antihalation dyes in photography.

It is another object of the present invention to provide a method of synthesizing p-N-alkylsulfonamidophenylhydrazines useful as intermediates in the synthesis of said bis-pyrazolone oxonol compounds.

Other objects of this invention will in part be obvious and will in part appear hereinafter.

The invention accordingly comprises the processes involving the several steps and the relation and order of one or more of such steps with respect to each of the others, which are exemplified in the following detailed disclosure, and the scope of the application of which will be indicated in the claims.

For a fuller understanding of the nature and objects of the present invention reference should be had to the following detailed description.

DESCRIPTION OF THE PREFERRED EMBODIMENTS

In one embodiment, the method of the present invention comprises:

(1) reacting (a) a p-N-alkylsulfonamidophenylhydrazine or its hydrochloride with (b) sodium diethyl oxalacetate in an inert, alkali-stable organic solvent to yield a 3-carbethoxy-1-(p-N-alkylsulfonamidophenyl)-2-pyrazolin-5-one;

(2) hydrolyzing said 3-carbethoxy-1-(p-N-alkylsulfonamidophenyl)-2-pyrazolin-5-one in situ with aqueous alkali to give the corresponding 3-carboxy-1-(p-N-alkylsulfonamidophenyl)-2-pyrazolin-5-one;

(3) reacting said 3carboxy-1-(p-N-alkylsulfonamidophenyl)-2-pyrazolin-5-one with a glycol having the formula HO(CH$_2$)$_m$OH wherein m is 2 or 3 in the presence of boron trifluoride etherate to yield the corresponding 3-carb($\beta$-hydroxy)alkoxy-1-(p-N-alkylsulfonamidophenyl)-2-pyrazolin-5-one; and (4) reacting said 3-carb($\beta$-hydroxy)alkoxy-1-(p-N-alkylsulfonamidophenyl)-2-pyrazolin-5-one and glutaconaldehyde dianil hydrochloride or malonaldehyde dianil hydrochloride in an inert, water-miscible organic solvent in the presence of a condensing agent to yield a compound having the formula

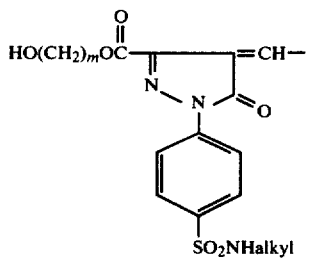

-continued

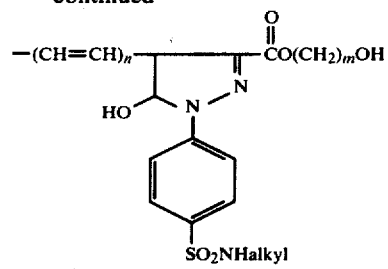

wherein m is 2 or 3 and n is 1 or 2.

In another embodiment of the present invention, the phenylhydrazine (a) employed in step (1) above is prepared by (A) reacting p-fluorobenzenesulfonyl chloride with a primary alkylamine in an inert organic solvent in the presence of an acid acceptor to give the corresponding 1-fluoro-4-N-p-alkylsulfonamidobenzene;

(B) reacting said 1-fluoro-4-N-p-alkylsulfonamidobenzene with hydrazine hydrate in an aprotic solvent to yield the corresponding p-N-alkylsulfonamidophenylhydrazine; and (C) converting said phenylhydrazine to its HCl salt.

The reaction scheme of the present method including the synthesis of the aforementioned phenylhydrazine is illustrated below.

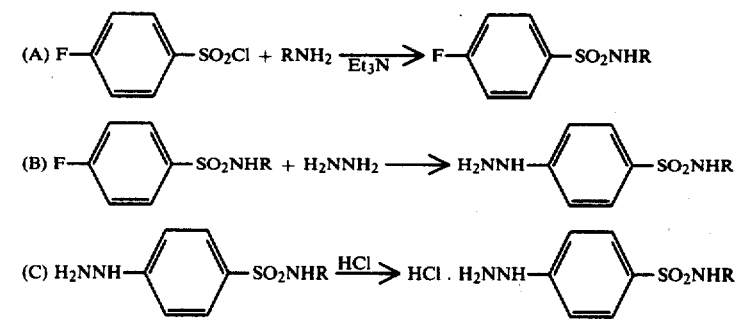

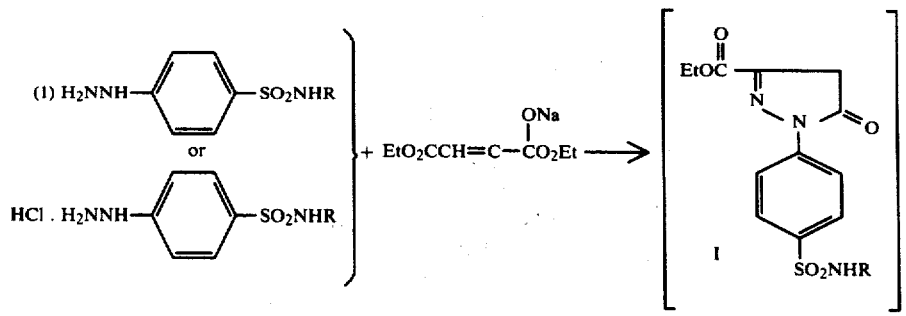

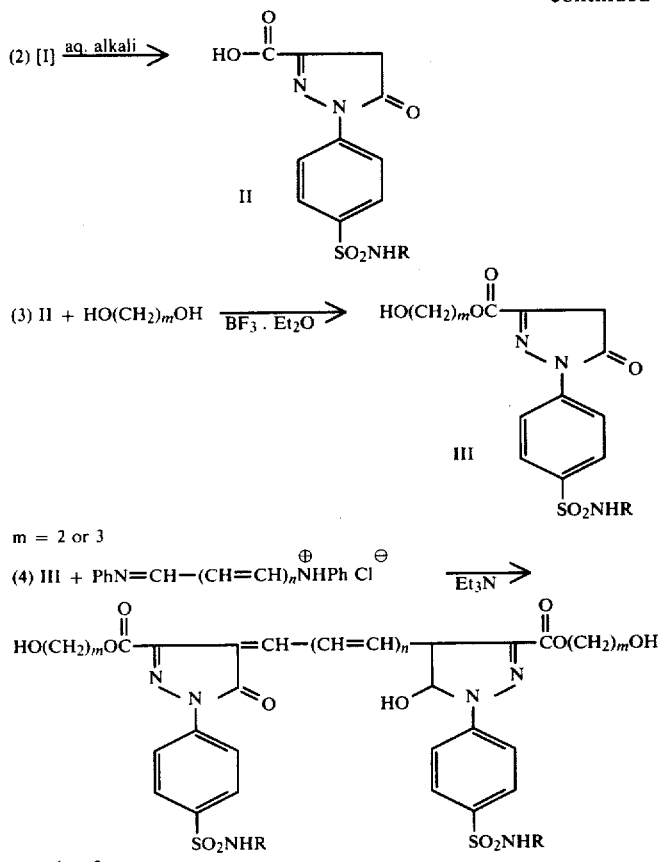

m = 2 or 3 n = 1 or 2

In preparing the phenylhydrazine reagent, p-fluorobenzenesulfonyl chloride and a primary alkylamine, $RNH_2$ wherein R is alkyl containing 1 to 12 carbon atoms and preferably n-alkyl, are reacted in an inert organic solvent at ambient temperature usually by adding a solution of the sulfonyl chloride in the solvent to a solution of the amine and an acid acceptor. The reaction proceeds spontaneously with an initial exotherm raising the temperature from room temperature (~20° C.) to about 70° C., and after a suitable period, the 1-fluoro-4-N-alkylsulfonamidobenzene is isolated by quenching into ice-water. The sulfonyl chloride and amine may be reacted in substantially equimolar proportions, but to ensure completion of the reaction, a 5–10% molar excess of the amine ordinarily is employed. The acid acceptor may be any of the materials commonly used for this purpose, for example, pyridine or triethylamine, and like the amine reactant is usually employed in a 5–10% molar excess based on the sulfonyl chloride.

The sulfonamide thus formed may be purified, e.g., by recrystallization from cyclohexane, but generally is used directly as isolated. Either way, the sulfonamide is reacted with an excess of about 5 to 10 mole equivalents of hydrazine hydrate in a dipolar aprotic solvent at a temperature between about 90° and 150° C. to give the corresponding p-N-alkylsulfonamidophenylhydrazine. The dipolar aprotic solvent may be any of those commonly employed, such as, dimethyl sulfoxide, dimethylformamide, dimethylacetamide, tetramethylene sulfone and hexamethyltriphosphoramide. Such solvents are well-known in the art, and in this regard, reference is made to Parker, Quart. Rev. (London), 16, 163 (1962). Because of higher conversion rates and lesser deterioration at higher temperatures, the use of dimethyl sulfoxide is preferred.

The phenylhydrazine also may be prepared by combining the two steps described above into a single operation. In the alternative "one-pot" procedure, the sulfonamide is synthesized in the same manner described above provided the inert organic solvent has a boiling point or boiling range not exceeding about 80° C., followed by the addition of dimethyl sulfoxide and the usual excess of hydrazine hydrate. The inert organic solvent is distilled away, and the reaction carried to its conclusion in the dimethyl sulfoxide to yield the phenylhydrazine. A major benefit of this alternative is the elimination of the isolation of the intermediate sulfonamide prior to reaction with the hydrazine hydrate.

Where the two steps are performed separately, the inert organic solvent preferably is water-miscible, for example, dimethoxyethane, and where the two steps are combined, the solvent can also be water-immiscible, for example, hexane. A particularly preferred solvent for use in both procedures is tetrahydrofuran.

The phenylhydrazine may be used directly for reaction with sodium diethyl oxalacetate, or it may be converted to its hydrochloride which is then reacted with the oxalacetate. The conversion to the hydrochloride may be carried out in a conventional manner, for example, by stirring the phenylhydrazine with a mixture of inert organic solvent and aqueous hydrochloric acid, removing the water and isolating the hydrochloride product by filtration. If the phenylhydrazine is to be stored prior to reaction with the oxalacetate, it should be stored as the hydrochloride to prevent degradation upon standing. Otherwise, it is most convenient to react the freshly prepared phenylhydrazine directly with the oxalacetate so that the step of converting to the hydrochloride may be omitted.

In preparing the bis-hydroxyalkyl ester pyrazolone oxonol dyes, step (1) of the present method is carried out by reacting (a) one mole of a p-N-alkylsulfonamidophenylhydrazine or its hydrochloride with a 10 to 20% molar excess of sodium diethyl oxalacetate at a temperature between about 50° and 100° C. in an inert organic solvent, preferably in the presence of a 10% to 20% molar excess of acetic acid. Because the 3-carbethoxy-1-(p-N-alkylsulfonamidophenyl)-2-pyrazolin-5-one formed is subsequently hydrolyzed in situ using aqueous alkali, the organic solvent employed should also be alkali-stable, and preferably is water-miscible. Suitable solvents include ethanol, acetonitrile and particularly, tetrahydrofuran. Though the use of acetic acid is not essential, it appears to catalyze the reaction as evidenced by a reduction in reaction time.

The 3-carbethoxypyrazolone ester thus formed is hydrolyzed by adding aqueous alkali to the reaction mixture in an excess over stoichiometric amounts. Usually, the reaction mixture is cooled to room temperature before alkali addition. Though any alkali metal or alkaline earth metal hydroxide may be employed, the hydrolysis is most conveniently carried out using about 1.2 to 2.0 moles of sodium hydroxide in 25% aqueous solution per mole of pyrazolone ester. The 3-carboxypyrazolone obtained as the hydrolysis product is isolated by quenching into cold water followed by acidification, and for achieving optimum results, the 3-carboxypyrazolone preferably is purified, e.g., via hot trituration with ethyl acetate prior to the subsequent esterification step.

As discussed above, one of the primary advantages of the subject method is the formation of a pyrazolone intermediate which may be readily isolated and easily purified prior to the final condensation with aldehyde dianil to produce the dye product. By using pure 3-carboxypyrazolone in the subsequent step of the synthesis, the 3-carb($\beta$-hydroxy)alkoxypyrazolone can be obtained in high purity thereby simplifying the final condensation reaction and the purification of the less stable dye product.

It will be appreciated that the synthesis of the 3-carboxy-1-(p-N-alkylsulfonamidophenyl)-2-pyrazolin-5-one may be accomplished in a continuous manner starting from p-fluorobenzenesulfonyl chloride by employing the "one-pot" procedure described above for preparing the phenylhydrazine, using the crude wetcake phenylhydrazine for reaction with the sodium diethyl oxalacetate to form the pyrazolone ethyl ester, and adding aqueous alkali to the reaction mixture comprising the ethyl ester to yield the corresponding 3-carboxypyrazolone. By proceeding in this manner, the need for isolating and drying the fluorobenzenesulfonamide intermediate and for converting the phenylhydrazine to its hydrochloride is eliminated. Because process times are very substantially reduced up to this point in the dye synthesis, the overall process time for preparing the dye product also is reduced and usually is less than half that of previous methods.

To form the hydroxyalkyl pyrazolone ester, the 3-carboxy-1-(p-N-alkylsulfonamidophenyl)-2-pyrazolin-5-one is reacted with a glycol of the formula HO(CH$_2$)$_m$OH wherein m is 2 or 3 in the presence of boron trifluoride-etherate catalyst at a temperature between about 60° and 100° C. The 3-carboxypyrazolone and glycol may be reacted in equivalent amounts, but usually about five to twenty-fold excess of glycol is employed to ensure completion of the esterification reaction. The boron trifluoride-etherate, although a catalyst, is employed in amounts equivalent to $\frac{1}{4}$ to $\frac{3}{4}$ that of the glycol employed. The resulting 3-carb($\beta$-hydroxy)alkoxy-1-(p-N-alkylsulfonamidophenyl)-2-pyrazolin-5-one is readily isolated in very high yields and purity by quenching into water and may be recrystallized, e.g., from iso-amyl or butyl acetate if desired.

The condensation reaction for producing the bis-hydroxyalkyl ester pyrazolone oxonol dyes is conducted by reacting the 3-carb($\beta$-hydroxy)alkoxy-1-(p-N-alkylsulfonamidophenyl)-2-pyrazolin-5-one and glutaconaldehyde dianil hydrochloride or malonaldehyde dianil hydrochloride in a stoichoimetric ratio of 2 moles of pyrazolone and 1 mole of dianil in an inert organic solvent in the presence of a condensing agent. Though the dianil may be used in an excess, for example, of up to about 10%, no substantial benefits are achieved in terms of yields or dye quality. Any condensing agent may be employed, for example, pyridine, pyrrolidine or triethanolamine but preferably, triethylamine is employed in amounts between about 1 and 6 moles and preferably, between about 3.5 and 4.5 moles per mole of dianil. The solvent preferably is water-miscible. Useful solvents include dimethyl sulfoxide, dimethylformamide, tetrahydrofuran, ethyl acetate, acetonitrile, dimethoxyethane and particularly, acetone. The reaction may be conducted at a temperature between about −20° C. and 25° C. and is most conveniently carried out at room temperature, i.e., ~20° C.

If it is desired to purify the bis-1,5-[3-carb($\beta$-hydroxy)alkoxy-1-(p-N-alkylsulfonamidophenyl)-2-pyrazolin-5-one]pentamethine oxonol dye products, the most satisfactory procedure involves converting the dye product to its sodium salt and then recrystallizing the salt. The dye product may be conveniently converted to its sodium salt by dissolution in acetone and stirring with a 10 molar excess of sodium bicarbonate. The resulting solution of the sodium salt is then easily filtered from the excess bicarbonate. Further purification may be accomplished by converting the dye salt to its non-salt form, heating the free dye to reflux in trifluoroethanol and stirring at room temperature for several hours before filtering to recover the product.

The following examples are given to further illustrate the present invention and are not intended to limit the scope thereof.

EXAMPLE 1

Synthesis of p-N-n-pentylsulfonamidophenylhydrazine and its hydrochloride:

(A) A solution containing 20 g. (0.10 mole) of p-fluorobenzenesulfonyl chloride in 25 ml. of tetrahydrofuran was added dropwise over a 10 minute period to a solution containing 9.5 g. (0.11 mole) of n-pentylamine and 11 g. (0.11 mole) of triethylamine with vigorous agitation. The resulting exotherm was allowed to proceed without cooling as the temperature rose to 70° C. After further stirring for five hours, the mixture was poured into ~1 liter of ice-water with rapid agitation. The product was filtered, washed with water and air dried at room temperature to give 24.7 g. (98% yield) of 1-fluoro-4-N-n-pentylsulfonamidobenzene as waxy off-white crystals (m.p. 51° C.).

(B) A solution containing 32 g. (0.13 mole) of 1-fluoro-4-N-n-pentylsulfonamidobenzene and 32 g. (0.65 mole) of hydrazine hydrate in 100 ml. of dimethyl sulfoxide were heated at 125° C. for 24 hours. The solution was cooled to room temperature and poured into ~1 liter of ice-water with rapid agitation. Filtration and washing with water followed by oven drying in-vacuo @ 40° C. gave 31 g. (93% yield) of the title compound as a white powder (m.p. 71° C.).

(C) A crude wet-cake of the phenylhydrazine obtained upon filtration of the reaction mixture as in Step B above was added to a mixture of 250 ml. of toluene and 35 ml. of 37% HCl with rapid agitation. The mixture was heated to about 90° C. as water was azeotropically removed. Upon complete removal of the water, the mixture was cooled to room temperature and the product filtered, washed with toluene and dried in-vacuo @ 60° C. to give 36 g. (94% yield) of p-N-n-pentylsulfonamidophenylhydrazine hydrochloride as off-white crystals.

EXAMPLE 2

Synthesis of p-N-n-pentylsulfonamidophenylhydrazine and its hydrochloride:

A solution containing 20 g. (0.10 mole) of p-fluorobenzenesulfonyl chloride in 25 ml. of hexane was added evenly over a 10 minute period to a well stirred solution containing 11 g. (0.11 mole) of triethylamine and 9.5 g. (0.11 mole) of n-pentylamine in 25 ml. of hexane. After stirring at room temperature for five hours, 100 ml. of dimethyl sulfoxide and 15 g. (0.30 mole) of hydrazine hydrate were added. The solution was heated and distillate collected until the temperature reached 120° C. After disconnecting the distillation head, an additional 15 g. (0.30 mole) of hydrazine hydrate was added and heating continued at 120°–125° C. for seven hours. The solution was allowed to cool to room temperature, then filtered and added to ~1 liter of ice-water with rapid agitation. The resulting white phenylhydrazine product was filtered, washed with water and immediately converted to the hydrochloride as described in Example 1 above. The overall yield of the title hydrochloride compound obtained as an off-white powder was 23 g. (78%). This material titrated at 99.7%.

EXAMPLE 3

Synthesis of bis-1,5-[3-carb($\beta$-hydroxy)ethoxy-1-(p-N-n-pentylsulfonamidophenyl)-2-pyrazolin-5-one]-pentamethine oxonol:

(1) A solution containing 26 g. (0.09 mole) of N-n-pentyl-p-sulfonamidophenylhydrazine hydrochloride, 21 g. (0.10 mole) of sodium diethyl oxalacetate and 6 g. (0.10 mole) of acetic acid in 150 ml. of tetrahydrofuran was heated at reflux for seven hours.

(2) After cooling to room temperature, 14 g. (0.35 mole) of sodium hydroxide in 25% aqueous solution was added. The mixture was stirred at room temperature for 24 hours then poured into 500 ml. of cold water. With rapid stirring, the solution was slowly acidified to pH 1 with concentrated HCl. The precipitated product was filtered, washed with water and dried in-vacuo @ 50° C. to give 30.3 g. (96% yield) of 3-carboxy-1-(p-N-n-pentylsulfonamidophenyl-2-pyrazolin-5-one (92% pure by titration) which was recrystallized as follows: A mixture containing 28 g. (0.08 mole) of the crude pyrazolonecarboxylic acid prepared above and 150 ml. of ethyl acetate was stirred at reflux for one hour then cooled to room temperature and filtered. The product was washed with ethyl acetate and air dried in-vacuo to give 25 g. (90% yield) of analytically pure pyrazolonecarboxylic acid.

(3) A mixture containing 1 g. (2.84 mmole) of the recrystallized pyrazolonecarboxylic acid of Step 2 and 3 ml. of ethylene glycol was stirred and heated at 80° C. until solution was effected. A total of 2 ml. of boron trifluorideetherate was added in several portions and the resulting solution heated at 80°–85° C. under a nitrogen atmosphere for 2.5 hours. After cooling to room temperature, the solution was poured into cold water and the precipitated product filtered, washed with water and dried in-vacuo @ 45° C. to give 1.1 g. (98% yield) of 3-carb($\beta$-hydroxy)ethoxy-1-(p-N-n-pentylsulfonamidophenyl)-2-pyrazolin-5-one; titration=99.0% purity. Quantitative TLC comparison showed <1% pyrazolonecarboxylic acid in the final product.

(4) To a mixture containing 10 g. (0.025 mole) of 3-carb($\beta$-hydroxy)ethoxy-1-(p-N-n-pentylsulfonamidophenyl)-2-pyrazolin-5-one (99.0% pure) and 3.6 g. (0.0126 mole) of glutaconaldehyde dianil hydrochloride in 100 ml. of acetone, 5 g. (0.050 mole) of triethylamine was added all at once. The resulting solution was stirred for one hour then poured into one liter of cold water with rapid agitation. The aqueous dye solution was then acidified to pH 1 with 10% w/w HCl. The precipitate was filtered, washed with water and oven dried in-vacuo @ 60° C. to give 10.7 g. (100% yield) of the title compound: $\lambda_{Max}^{MeCell}$ 666 m$\mu$; $\epsilon$=138,000.

As discussed above, the bis-pyrazolone oxonol dyes produced in accordance with the subject method may be purified by forming the sodium salt of the dye, recrystallizing the dye salt and then recrystallizing the free dye as illustrated below:

A solution containing 5 g. (5.8 mmole) of bis-1,5-[3-carb($\beta$-hydroxy)ethoxy-1-(p-N-n-pentylsulfonamidophenyl)-2-pyrazolin-5-one]-pentamethine oxonol ($\lambda_{Max}^{MeCell}$ 666 m$\mu$=130,000) in 25 ml. of acetone was mixed with 5 g. (59 mmole) of sodium bicarbonate and the mixture stirred at room temperature for one hour. After filtering off the excess bicarbonate, the filtrate was added dropwise to 250 ml. of toluene with rapid agitation over a period of 10 minutes. The granular product was filtered and air dried ($\lambda_{Max}^{MeCell}$ 666 m$\mu$=137,000).

A solution containing 5 g. (5.8 mmole) of bis-1,5-[3-carb($\beta$-hydroxy)ethoxy-1-p-N-n-pentylsulfonamidophenyl)-2-pyrazolin-5-one]-pentamethine oxonol in 25 ml. of trifluoroethanol was heated to reflux and then allowed to stir overnight at room temperature. The product was filtered, washed with a little trifluoroethanol and dried at room temperature to give 2.7 g. (54% yield) of 100% pure dye product. ($\lambda_{Max}^{MeCell}$ 666 m$\mu$=155,000). Dye recovery based on = was equivalent to 60% yield.

The bis-pyrazolone oxonol dyes also were prepared by employing the non-stop procedure described above for producing the 3-carboxy-1-(p-N-alkylsulfonamidophenyl)-2-pyrazolin-5-one followed by esterification and condensation in the usual manner to yield the dye product.

EXAMPLE 4

Synthesis of bis-1,5-[3-carb($\beta$-hydroxy)ethoxy-1-(p-N-n-pentylsulfonamidophenyl)-2-pyrazolin-5-one]-pentamethine oxonol:

A solution containg 200 g. (1.03 mole) of p-fluorobenzenesulfonyl chloride in 250 ml. of hexane was added at a steady rate to a well stirred solution containing 110 g. (1.09 moles) of triethylamine and 96 g. (1.1 moles) of n-pentylamine in 250 ml. of hexane over a period of 15 minutes. After stirring for five hours, 1 liter of dimethyl sulfoxide and 150 g. (3.0 moles) of hydrazine hydrate were added. The solution was heated and distillate collected until the temperature reached 120° C. After disconnecting the distillation head, an additional 150 g. (3.0 moles) of hydrazine hydrate was added and heating continued at 120°-126° C. for seven hours. After cooling to room temperature, the solution was filtered and added to ~10 l of ice-water with rapid agitation. The resulting white N-n-pentyl-p-sulfonamidophenylhydrazine was filtered and washed with water using a rubber dam over the cake to remove as much moisture as possible. The wet-cake (ca. 70% solids) was added to a mixture containing 231 g. (1.1 moles) of sodium diethyl oxalacetate and 75 g. (1.25 moles) of acetic acid in 1 liter of tetrahydrofuran. The resulting solution was heated at reflux (67° C.) for seven hours, cooled to 50° C. and 160 g. (4 moles) of sodium hydroxide in 25% wt/wt aqueous solution added. After stirring for 2 hours at 50°-60° C., the mixture was poured into ~7 l of cold water and slowly acicified to ~pH 1 by dropwise addition of 10% w/w HCl. The product was filtered, washed thoroughly with water and oven dried in-vacuo @ 50° C. to give 288 g. of crude 3-carboxy-1-(p-N-n-pentylsulfonamidophenyl)-2-pyrazolin-5-one. Overall content yield from the starting p-fluorobenzenesulfonyl chloride was 71% (89% purity by titration). Purification via trituration with ethyl acetate (5 ml/g) as described in Example 3 above gave the pyrazolone carboxylic acid in 60% overall content yield (220 g.) with 98.8% purity.

The subsequent steps of esterifying the pyrazolonecarboxylic acid with ethylene glycol and condensing the glycol pyrazolone ester with glutaconaldehyde dianil hydrochloride were carried out in the same manner as described in Example 3 above to give the title compound.

The percentage yield and percentage purity given in the above Examples is on a weight basis.

It will be appreciated that different solvents, acid acceptors, condensing agents and alkaline solutions may be substituted for those used in the foregoing Examples and also that 1,3-propanediol, malonaldehyde dianil hydrochloride and other alkylamines may be used in the procedures of the foregoing Examples to yield oxonol dye products having the formula:

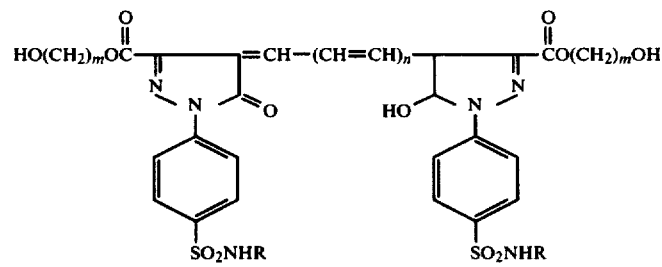

wherein R is alkyl containing 1 to 12 carbon atoms, preferably n-alkyl, m is an integer 2 or 3 and n is an integer 1 or 2.

Since certain changes may be made in the hereindescribed subject matter without departing from the scope of the invention herein involved, it is intended that all matter contained in the above description and examples be interpreted as illustrative and not in a limiting sense.

What is claimed is:

1. A method of preparing a bis-pyrazolone oxonol compound which comprises:
   (1) reacting (a) a p-N-alkylsulfonamidophenylhydrazine or its hydrochloride with (b) about a 10 to 20% molar excess of sodium diethyl oxalacetate in an inert, alkali-stable organic solvent at a temperature between about 50° and 100° C. to yield a 3-carbethoxy-1-(p-N-alkylsulfonamidophenyl)-2-pyrazolin-5-one;
   (2) hydrolyzing said 3-carbethoxy-1-(p-N-alkylsulfonamidophenyl)-2-pyrazolin-5-one in situ with aqueous alkali at room temperature to give the corresponding 3-carboxy-1-(p-N-alkylsulfonamidophenyl)-2-pyrazolin-5-one;
   (3) removing substantially all of the impurities from said 3-carboxy-1-(p-N-alkylsulfonamidophenyl)-2-pyrazolin-5-one;
   (4) reacting said purified 3-carboxy-1-(p-N-alkylsulfonamidophenyl)-2-pyrazolin-5-one with a five to twenty-fold amount of a glycol having the formula $HO(CH_2)_mOH$ wherein m is 2 or 3 in the presence of boron trifluoride-etherate at a temperature between about 50° and 100° C. to yield the corresponding 3-carb($\beta$-hydroxy)alkoxy-1-(p-N-alkylsulfonamidophenyl)-2-pyrazolin-5-one; and
   (5) reacting said 3-carb($\beta$-hydroxy)alkoxy-1-(p-N-alkylsulfonamidophenyl)-2-pyrazolin-5-one with a stoichiometric amount of glutaconaldehyde dianil hydrochloride or malonaldehyde dianil hydrochloride at a temperature between about −20° and 25° C. in an inert organic solvent in the presence of a condensing agent to yield a bis-pyrazolone oxonol compound having the formula

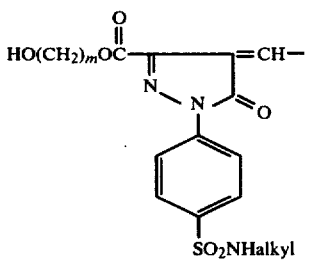

-continued

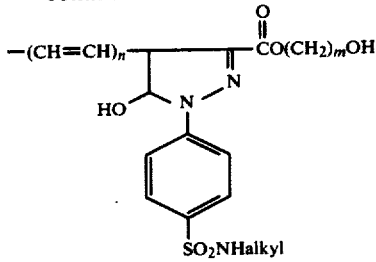

wherein m is an integer 2 or 3 and n is an integer 1 or 2.

2. A method as defined in claim 1 wherein said alkyl of said p-N-alkylsulfonamidophenylhydrazine (a) contains 1 to 12 carbon atoms.

3. A method as defined in claim 1 wherein said (a) is a p-N-alkylsulfonamidophenylhydrazine hydrochloride.

4. A method as defined in claim 1 wherein said (a) is a p-N-alkylsulfonamidophenylhydrazine.

5. A method as defined in claim 1 wherein said inert, alkali-stable organic solvent employed in step (1) is tetrahydrofuran.

6. A method as defined in claim 1 wherein said aqueous alkali employed in step (2) is 25% aqueous sodium hydroxide.

7. A method as defined in claim 1 wherein said inert, organic solvent employed in step (4) is water-miscible.

8. A method as defined in claim 7 wherein said solvent is acetone.

9. A method as defined in claim 1 wherein said condensing agent employed in step (4) is triethylamine.

10. A method as defined in claim 1 wherein said bis-pyrazolone oxonol compound has the formula

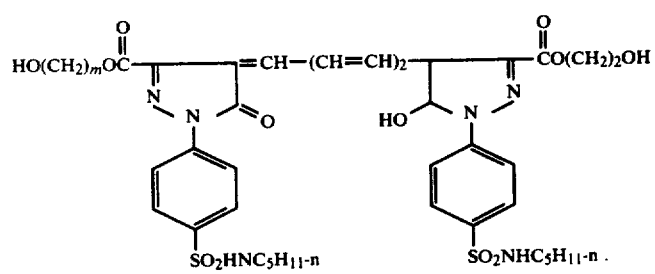

11. A method as defined in claim 3 which additionally includes the steps of preparing said p-N-alkylsulfonamidophenylhydrazine hydrochloride by
(A) reacting p-fluorobenzenesulfonyl chloride with an equimolar amount or up to about a 10% molar excess of a primary alkylamine in an inert organic solvent at room temperature in the presence of an acid acceptor to yield the corresponding 1-fluoro-4-N-alkylsulfonamidobenzene;
(B) reacting said 1-fluoro-4-N-alkylsulfonamidobenzene with an excess of about 5 to 10 mole equivalents of hydrazine hydrate in an aprotic solvent at a temperature between about 90° and 150° C. to yield the corresponding p-N-alkylsulfonamidophenylhydrazine; and
(C) converting said hydrazine to its hydrochloride by reacting said p-N-alkylsulfonamidophenylhydrazine with a solution of hydrochloric acid at room temperature.

12. A method as defined in claim 11 wherein said inert organic solvent is tetrahydrofuran.

13. A method as defined in claim 11 wherein said acid acceptor is triethylamine.

14. A method as defined in claim 11 wherein said aprotic solvent is dimethyl sulfoxide.

15. A method as defined in claim 4 which includes the additional steps of preparing said p-N-alkylsulfonamidophenylhydrazine by
(A) reacting p-fluorobenzenesulfonyl chloride with an equimolar amount or up to about a 10% molar excess of a primary alkylamine in an inert organic solvent at room temperature in the presence of an acid acceptor to yield the corresponding 1-fluoro-4-N-alkylsulfonamidobenzene and
(B) reacting said 1-fluoro-4-N-alkylsulfonamidobenzene with an excess of about 5 to 10 mole equivalents of hydrazine hydrate in an aprotic solvent at a temperature between about 90° and 150° C. to yield the corresponding p-N-alkylsulfonamidophenylhydrazine.

16. A method as defined in claim 15 wherein said inert organic solvent is water-miscible.

17. A method as defined in claim 16 wherein said inert organic solvent is tetrahydrofuran.

18. A method as defined in claim 15 wherein said acid acceptor is triethylamine.

19. A method as defined in claim 15 wherein said aprotic solvent is dimethyl sulfoxide.

20. A method as defined in claim 4 which includes preparing said p-N-alkylsulfonamidophenylhydrazine by reacting p-fluorobenzenesulfonyl chloride with an equimolar amount or up to about a 10% molar excess of a primary alkylamine in an inert organic solvent having a boiling point or boiling range not exceeding about 80° C. at room temperature in the presence of an acid acceptor to yield the corresponding 1-fluoro-4-N-alkylsulfonamidobenzene, adding an excess of about 5 to 10 moles of hydrazine hydrate in dimethyl sulfoxide, removing said inert organic solvent by distillation and heating said reaction mixture at a temperature between about 90° and 150° C. to yield the corresponding p-N-alkylsulfonamidophenylhydrazine.

21. A method as defined in claim 20 wherein said inert organic solvent is hexane.

22. A method as defined in claim 20 wherein said inert organic solvent is tetrahydrofuran.

23. A method as defined in claim 20 wherein said acid acceptor is triethylamine.

24. A method as defined in claim 1 wherein said (a) and (b) are reacted in the presence of a 10 to 20% molar excess of acetic acid as based on 1 mole of said (a).

25. A method of preparing a p-N-alkylsulfonamidophenylhydrazine by (A) reacting p-fluorobenzenesulfonyl chloride with an equimolar amount or up to about a 10% molar excess of a primary alkylamine in an inert organic solvent at room temperature in the presence of an acid acceptor to yield the corresponding 1-fluoro-4-N-alkylsulfonamidobenzene and (B) reacting said 1-fluoro-4-N-alkylsulfonamidobenzene with an excess of about 5 to 10 moles of hydrazine hydrate in an aprotic solvent at a temperature between about 90° and 150° C. to yield the corresponding p-N-alkylsulfonamidophenylhydrazine.

26. A method as defined in claim 25 wherein said inert organic solvent is water-miscible.

27. A method as defined in claim 26 wherein said inert organic solvent is tetrahydrofuran.

28. A method as defined in claim 25 wherein said acid acceptor is triethylamine.

29. A method as defined in claim 25 wherein said aprotic solvent is dimethyl sulfoxide.

30. A method of preparing a p-N-alkylsulfonamidophenylhydrazine by reacting p-fluorobenzenesulfonyl chloride with an equimolar amount or up to about a 10% molar excess of a primary alkylamine in an inert organic solvent having a boiling point or boiling range not exceeding about 80° C. at room temperature in the presence of an acid acceptor to yield the corresponding 1-fluoro-4-N-alkylsulfonamidobenzene, adding an excess of about 5 to 10 moles of hydrazine hydrate in dimethyl sulfoxide, removing said inert organic solvent by distillation and heating said reaction mixture at a temperature between about 90° and 150° C. to yield the corresponding p-N-alkylsulfonamidophenylhydrazine.

31. A method as defined in claim 30 wherein said inert organic solvent is hexane.

32. A method as defined in claim 30 wherein said inert organic solvent is tetrahydrofuran.

33. A method as defined in claim 30 wherein said acid acceptor is triethylamine.

* * * * *